United States Patent
Krauss et al.

(10) Patent No.: US 8,800,350 B2
(45) Date of Patent: Aug. 12, 2014

(54) PARTICLE SENSOR

(75) Inventors: Andreas Krauss, Tuebingen (DE); Tino Fuchs, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 650 days.

(21) Appl. No.: 12/941,484

(22) Filed: Nov. 8, 2010

(65) Prior Publication Data

US 2011/0107817 A1    May 12, 2011

(30) Foreign Application Priority Data

Nov. 6, 2009  (DE) .................. 102009046457 U

(51) Int. Cl.
*G01N 25/18* (2006.01)
*G01R 27/08* (2006.01)
*G01N 27/18* (2006.01)
*G01N 15/06* (2006.01)
*G01N 27/04* (2006.01)

(52) U.S. Cl.
CPC ............... *G01N 27/04* (2013.01); *G01N 27/18* (2013.01); *G01N 15/0656* (2013.01)
USPC .......................................... 73/25.03; 324/693

(58) Field of Classification Search
USPC .......................................... 73/25.03; 324/693
See application file for complete search history.

(56) References Cited

U.S. PATENT DOCUMENTS

2010/0312488 A1 * 12/2010 Diehl et al. .................. 702/23

FOREIGN PATENT DOCUMENTS

| CN | 1236097 | 11/1999 |
|---|---|---|
| CN | 101001767 | 7/2007 |
| CN | 100410657 | 8/2008 |
| CN | 101294890 | 10/2008 |
| DE | 101 33 384 | 1/2003 |
| DE | 101 56 946 | 5/2003 |
| EP | 703449 A1 * | 3/1996 |
| EP | 2 128 597 | 12/2009 |
| WO | WO 03/006976 | 1/2003 |
| WO | WO 2006/027287 | 3/2006 |
| WO | WO 2006/077197 | 7/2006 |
| WO | WO 2008/138849 | 11/2008 |

* cited by examiner

*Primary Examiner* — Hezron E Williams
*Assistant Examiner* — Gregory J Redmann
(74) *Attorney, Agent, or Firm* — Kenyon & Kenyon LLP

(57) ABSTRACT

A particle sensor including a diaphragm, a diaphragm heater, and at least two measuring electrodes situated on the diaphragm, for electrical conductivity measurement, the diaphragm having a thickness of less than or equal to 50 μm, in order to allow a calorimetric particle quantity determination.

6 Claims, 1 Drawing Sheet

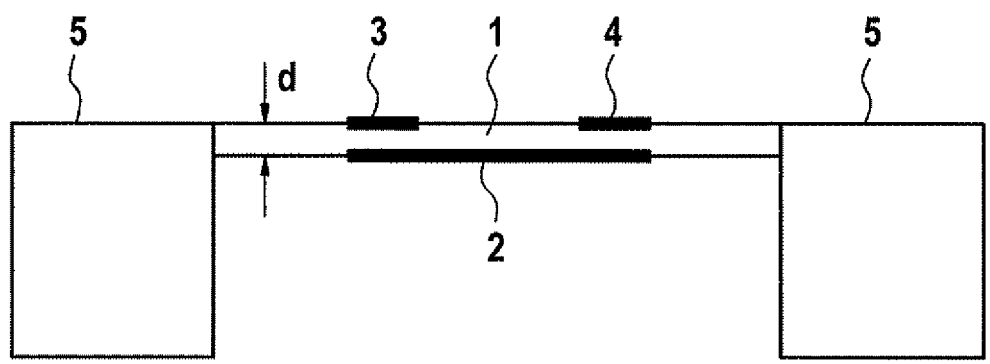

PARTICLE SENSOR

FIELD OF THE INVENTION

The present invention relates to a particle sensor and a method for the operation thereof.

BACKGROUND INFORMATION

In addition to optical methods for particle measurement, particle sensors are known, which measure the particle content in an exhaust gas via a conductivity measurement of particles accumulated on a surface between two measuring electrodes. In order to minimize the influence of condensed moisture on the conductivity, for example, these conductivity measurements are performed at a higher, constant temperature. Then, such particle sensors are periodically regenerated by thermal and/or electrical methods, in which accumulated particles are removed by so-called "burn off."

The precision of the measurement is typically limited, in particular after the regeneration and in the case of detection of small particle quantities, because particle bridges must first form between the measuring electrodes for the conductivity measurement.

German Patent Application No. DE 101 33 384 describes a particle sensor, which has a carrier layer having an integrated heating element as well as a second layer having printed-on measuring electrodes.

SUMMARY OF THE INVENTION

An object of the present invention is to provide a particle sensor for the detection of particles in a gas stream, in particular soot particles, for example in an exhaust gas stream, including a diaphragm, a diaphragm heater, and at least two measuring electrodes, which are situated on the diaphragm, for the electrical conductivity measurement, the diaphragm having a thickness of less than or equal to 50 μm.

A diaphragm is understood in particular to be a mechanically stable, thin layered carrier element.

Because of the small thickness of the diaphragm, its proportion of the total heated mass is advantageously decreased, whereby the proportion of the particles of the total heated mass is in turn proportionally increased and a calorimetric determination of the particle quantity is made possible. The precision of the particle sensor may in turn be improved and the cross-sensitivity of the particle sensor in relation to environmental influences such as moisture may be decreased.

The diaphragm is preferably implemented from a material having a high temperature stability and a low electrical conductivity.

The diaphragm may have a thickness of less than or equal to 40 μm, for example less than or equal to 20 μm or less than or equal to 10 μm. For example, the diaphragm may have a thickness of ≥1 μm to ≤20 μm, in particular ≥5 μm to ≤10 μm. Such thicknesses have proven to be advantageous, on the one hand, for achieving a suitable mechanical stability of the diaphragm and, on the other hand, for achieving the lowest possible heat capacity.

To further decrease the heat capacity, the diaphragm may additionally be microstructured. For example, the diaphragm may have openings to decrease the heat capacity and/or reinforced areas to increase the mechanical stability.

The diaphragm may be constructed from multiple layers. In other words, the diaphragm may be implemented as a layer system. For example, the diaphragm may include one or multiple carrier layers, and/or one or multiple insulation layers and/or one or multiple functional layers, for example layers in which a heating element and/or a sensor element, such as a temperature sensor or a thermal conductivity sensor, are integrated. The thickness of the diaphragm corresponds in particular to the thickness of the entire layer system.

In one specific embodiment of the particle sensor, the diaphragm includes silicon carbide (SiC). Being a material with a high temperature stability, silicon carbide has proven itself to be advantageous for implementing the diaphragm. For example, the diaphragm may be implemented entirely from silicon carbide. However, it is also possible that the diaphragm is constructed from multiple layers, of which at least one layer includes silicon carbide or is implemented therefrom.

The diaphragm heater may be integrated into the diaphragm as well as be implemented on the surface of the diaphragm.

In another specific embodiment, the diaphragm heater is integrated into the diaphragm. For example, the diaphragm may be constructed from multiple layers, of which one layer, an intermediate layer in particular, includes the diaphragm heater. In this way, measuring electrode systems, each including at least two measuring electrodes for the electrical conductivity measurement, may be situated on both main surfaces of the diaphragm. In particular, differently designed measuring electrode systems, for example measuring electrode systems having differing measuring electrode spacing, may be situated on the two main surfaces of the diaphragm. Additionally or alternatively thereto, other sensor elements, such as temperature sensors and/or mass flow sensors and/or thermal conductivity sensors, may be situated on the two main surfaces of the diaphragm.

In another specific embodiment, the diaphragm heater is implemented on the diaphragm surface. In particular, the diaphragm heater may be implemented on one main surface of the diaphragm, the measuring electrodes being implemented on the diametrically opposing main surface of the diaphragm.

The measuring electrodes are implemented in particular for performing an electrical conductivity measurement, for example, for performing a frequency-dependent impedance measurement, of particles accumulated between the measuring electrodes, on the diaphragm in particular. For example, the measuring electrodes may be implemented in the form of interlocking, comb-like electrodes, and form a so-called interdigital measuring electrode system. The spacings of the electrodes and their lengths may be adapted for various measuring ranges of soot particle quantities. Preferably, spacings between the electrodes of ≥1 μm to ≤100 μm are implemented.

The diaphragm may be suspended by a substrate. A dissipation of heat into other areas of the sensor during heating may be reduced in this way. For example, the diaphragm may be suspended by the substrate on at least two points, in particular diametrically opposing points. The substrate may also be implemented from a material having a high temperature stability. For example, the substrate may include silicon carbide (SiC) or be made therefrom. The analysis circuit and electronics of the sensor may be integrated into the substrate. The advantage thereof is that the number of electrical terminals to the outside may be reduced and thus the construction and connection technology may be simplified.

In another specific embodiment of the particle sensor, the diaphragm surface catalyzes the decomposition and/or combustion of particles, in particular soot particles. This process may be guaranteed by suitable selection of the diaphragm material and/or by a diaphragm coating made of a catalytically active material. In this case, the catalytically active diaphragm material or the catalytically active diaphragm coating is, in addition, preferably electrically insulating.

In another specific embodiment of the particle sensor, the sensor has two or more, in particular three or more units each having at least two measuring electrodes for the electrical conductivity measurement positioned on a diaphragm and a diaphragm heater, for heating the measuring electrodes of the unit in particular. In this case, the diaphragm heaters may also be integrated into the diaphragm, as already explained, or situated on the surface of the diaphragm.

Fundamentally, the measuring electrodes and the diaphragm heaters of the individual units may be implemented spaced apart from one another on or in a shared diaphragm. In order to avoid measuring errors caused by heat flow, however, each unit preferably has its own diaphragm, in particular having a thickness of less than or equal to 50 µm.

Such units may advantageously be operated at various temperatures, which may have an advantageous effect on the sensitivity of the particle sensor. In particular, multiple units allow a better time resolution of the measurement. Thus, for example, multiple units may always be in the particle accumulation mode, while one other unit is in the particle measuring mode and determines the accumulated particle quantity with the aid of a conductivity measurement and/or a calorimetric measurement and is furthermore optionally freed of accumulated particles, partially or completely.

In another specific embodiment of the particle sensor, each of the diaphragm surfaces of the individual units has a different catalytic activity. For example, the diaphragm surfaces may catalyze the decomposition and/or combustion of particles, in particular soot particles, to varying extents. This fact may result in different decomposition and/or combustion temperatures of particles, for example, which in turn may have an advantageous effect on the determination of the composition of the gas stream.

As already explained, additional sensor functions may be integrated into the particle sensor. For example, the diaphragm heater may also be used to set a defined temperature via a specific temperature-dependent resistance characteristic. As a further example, the sensor may include one or multiple temperature sensors for determining the diaphragm temperature and/or the ambient temperature, and/or one or multiple mass flow sensors for determining the mass flow of the gas stream, and/or one or multiple thermal conductivity sensors for determining the thermal conductivity of the gas stream. In this way, for example, further statements about the composition of the gas stream, such as the carbon dioxide content and/or moisture content of the gas stream, may be made from the results of thermal conductivity measurements during the passage through a temperature profile.

The present invention also relates to a method for operating a particle sensor according to the invention, in which particles are accumulated in the particle accumulation mode and the accumulated particle quantity is determined by an electrical conductivity measurement and/or a calorimetric measurement in the particle measuring mode.

With the aid of the calorimetric measurement, in particular the combustion heat and/or decomposition heat of accumulated particles, in particular soot particles, may be determined. The calorimetric measurement may be based on a simultaneous measurement of the heat output and diaphragm temperature. Here, the diaphragm temperature may either be determined by the diaphragm heater or by an additional diaphragm temperature sensor. In particular, it is possible to pass through a heating profile during the calorimetric measurement. During the passage through the heating profile, temperatures at which accumulated particles, in particular soot particles, combust and/or decompose are expediently reached. A diaphragm structure has the advantage that the temperature may be modulated very rapidly. Such a calorimetric measurement is not possible in the case of conventional particle sensors because of the very small proportion of the particles in the total heated mass. Through the use of a diaphragm according to the present invention, the proportion of the sensor structure in the total heated mass is decreased, causing the proportion of the particles in the total heated mass to rise proportionally.

In order to make the particle determination more precise, the accumulated particle quantity may be determined by a combination of calorimetric, thermal, and electrical measurements in the particle measuring mode.

In another specific embodiment of the method, an electrical conductivity measurement and/or thermal conductivity measurement is performed as a function of a temperature profile. During the passage through a temperature profile—for example, at low temperatures—the electrical conductivity and/or thermal conductivity of accumulated substances—other than the particles to be determined—such as moisture and/or liquids made up of smoke droplets, may also be measured. The particle quantity may optionally indirectly be determined from the data thus acquired, which provide information about the degree of moisture in the particle layer, for example.

In another specific embodiment of the method, the accumulated particle quantity is determined indirectly from the results of electrical conductivity measurements and/or thermal conductivity measurements of accumulated substances other than the particles to be determined.

At higher temperatures, the other accumulated substances, such as moisture and/or liquids made up of smoke droplets, are expelled, so that the conductivity is determined as in conventional particle sensors by the accumulated particle quantity.

In addition, at least a part of the further composition of the gas stream, such as the moisture content of the gas stream, may advantageously be determined via the measurement of established temperature ranges. For example, at least a part of the further composition of the gas stream, such as the carbon dioxide content and/or the moisture content of the gas stream, may be determined via the electrical conductivity measurement and/or thermal conductivity measurement as a function of the temperature profile.

A regeneration of the particle sensor, i.e., freeing of the particle sensor from the accumulated particles, the so-called "burn off," may be performed both in the scope of the particle measuring mode and also in the scope of a following regeneration mode.

Since a rapid temperature control of the diaphragm is possible, accumulated particles may be removed not only completely, but rather even to the extent that only a defined residue remains, in particular by heating, while simultaneously measuring the electrical conductivity. In other words, the accumulated particles may be partially removed in such a way that a minimum amount of particle bridges is maintained between the measuring electrodes. In this way, a minimum amount of particle bridges between the measuring electrodes and thus an established electrical basic conductivity and an established electrical basic resistance may be maintained. This has the advantage that a renewed particle accumulation may continue to be measured immediately via a change in electrical conductivity or a change in electrical resistance, without conductivity bridges first having to form between the measuring electrodes, which may be time-consuming in particular in the case of small particle concentrations.

In another specific embodiment of the method, the particle sensor has two or more units already explained, one unit being in the particle measuring mode, while one or multiple other units are in the particle accumulation mode.

BRIEF DESCRIPTION OF THE DRAWING

FIG. 1 shows a schematic cross-section through a specific embodiment of a particle sensor according to the present invention.

DETAILED DESCRIPTION

FIG. 1 shows that the particle sensor includes a diaphragm 1, a diaphragm heater 2 situated on diaphragm 1, and two measuring electrodes 3, 4 situated on diaphragm 1, for the electrical conductivity measurement. Diaphragm heater 2 and measuring electrodes 3, 4 are situated on diametrically opposing sides of diaphragm 1 in the specific embodiment shown. FIG. 1 further shows that diaphragm 1 is suspended by a substrate 5 on two diametrically opposing points.

What is claimed is:

1. A particle sensor for a detection of particles in a gas stream, comprising:
   a diaphragm, the diaphragm having a thickness of less than or equal to 50 μm;
   a diaphragm heater; and
   at least two measuring electrodes, which are situated on the diaphragm, for electrical conductivity measurement.

2. The particle sensor according to claim 1, wherein the diaphragm includes silicon carbide.

3. The particle sensor according to claim 1, wherein the diaphragm heater is integrated into the diaphragm, or is situated on a surface of the diaphragm.

4. The particle sensor according to claim 1, wherein a surface of the diaphragm catalyzes a decomposition and/or combustion of particles, including soot particles.

5. The particle sensor according to claim 1, wherein the sensor has at least two units each having at least two measuring electrodes, which are situated on a diaphragm, for electrical conductivity measurement and a diaphragm heater.

6. The particle sensor according to claim 5, wherein diaphragm surfaces of individual units have different catalytic activities.

* * * * *